United States Patent
Urtel et al.

(10) Patent No.: US 7,847,129 B2
(45) Date of Patent: Dec. 7, 2010

(54) METHOD FOR DEHYDROGENATING ALCOHOLS

(75) Inventors: Heiko Urtel, Mannheim (DE); Soo Yin Chin, Mannheim (DE); Thorsten Johann, Ludwigshafen (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 12/307,925

(22) PCT Filed: Jul. 9, 2007

(86) PCT No.: PCT/EP2007/056940

§ 371 (c)(1),
(2), (4) Date: Jan. 8, 2009

(87) PCT Pub. No.: WO2008/006792

PCT Pub. Date: Jan. 17, 2008

(65) Prior Publication Data

US 2009/0312581 A1    Dec. 17, 2009

(30) Foreign Application Priority Data

Jul. 11, 2006    (EP)    ................... 06116987

(51) Int. Cl.
*C07C 45/27* (2006.01)
*C07C 45/29* (2006.01)

(52) U.S. Cl. ................ 568/403; 568/485; 568/487

(58) Field of Classification Search ................ 568/403, 568/485, 487
See application file for complete search history.

(56) References Cited

U.S. PATENT DOCUMENTS

| 2,794,053 | A | | 5/1957 | Altreuter et al. |
| 3,420,783 | A | | 1/1969 | Bergstrand |
| 4,655,891 | A | * | 4/1987 | Ward et al. ............. 204/157.93 |
| 4,891,446 | A | | 1/1990 | Slaugh |
| 7,495,132 | B2 | | 2/2009 | Walsdorff et al. |

FOREIGN PATENT DOCUMENTS

| DE | 1 282 611 | 11/1968 |
| WO | 2005 073157 | 8/2005 |

OTHER PUBLICATIONS

Weissermel, et al., Industrielle Organische Chemie, vol. 5, pp. 186-187, 1998.

* cited by examiner

*Primary Examiner*—Sikarl A Witherspoon
(74) *Attorney, Agent, or Firm*—Oblon, Spivak, McClelland, Maier & Neustadt, L.L.P.

(57) ABSTRACT

A method for dehydrogenating primary or secondary alcohols having 1 to 12 carbon atoms to give the corresponding aldehydes or ketones in which the alcohol is brought into contact with a catalytically active composition comprising an active component of the formula $$Pd_aBi_bY_cZ_d,$$

where
Y is selected from the group consisting of Co, Rh, Pt, Ag, Au, and
Z is selected from the group consisting of Na, Cs, Mg, Ca, Ba, V, Cr, W, Fe, Ni, Cu, Sb where the indices a, b, c and d give the mass ratios of the respective elements to one another, where
a=0.1-3,
b=0.1-3,
c=0-3,
d=0-1.

12 Claims, No Drawings

METHOD FOR DEHYDROGENATING ALCOHOLS

The invention relates to a method for dehydrogenating primary and secondary alcohols to give the corresponding aldehydes and ketones respectively.

Acetaldehyde may be produced by catalytic dehydrogenation of ethanol. On an industrial scale this is carried out as described in Weissermel, Arpe: Industrielle Organische Chemie [Industrial Organic Chemistry], 5th edition 1998, pp. 186-187, dehydrogenation in the presence of silver or copper catalysts, and also oxidative dehydrogenation in the presence of silver catalysts and oxygen.

The dehydrogenation is carried out at temperatures of 270 to 300° C., for example in the presence of copper catalysts which are activated by Zn, Co or Cr. At an ethanol conversion rate of 30 to 50%, a selectivity to acetaldehyde of 90 to 95% is achieved. By-products formed are ethyl acetate, crotonaldehyde, higher alcohols and ethylene.

In the case of oxidative dehydrogenation in the presence of air or oxygen, the simultaneous combustion of the hydrogen formed provides the required heat of dehydrogenation. Industrially, oxidative dehydrogenation is carried out in the presence of silver catalysts in the form of wire meshes or crystal packings. Ethanol, for example in a mixture with air, is passed over the catalyst at 3 bar and 450 to 550° C. The ethanol conversion rate is 30 to 50%, the selectivity to acetaldehyde 85 to 95%. By-products are acetic acid, formic acid, ethyl acetate, CO and $CO_2$.

Correspondingly, formaldehyde is prepared industrially by dehydrogenation or oxidative dehydrogenation of methanol in the presence of copper or silver catalysts.

In the Wacker-Hoechst method, by which 85% of worldwide acetaldehyde production is produced, as catalyst, use is made of a two-component system comprising $PdCl_2$ and $CuCl_2$. $PdCl_2$ which selectively oxidizes ethylene stoichiometrically to acetaldehyde, acts as the actual catalyst, $PdCl_2$ being reduced to the metal. The $CuCl_2$ cocatalyst subsequently oxidizes the metallic zero valent Pd back to the divalent state. The method is carried out as a single-stage or two-stage two-phase gas/liquid process, reaction and reoxidation of the platinum catalyst being carried out together in a single reactor, or separately in two reactors. The single-stage process is carried out at 120 to 130° C. at 3 bar with a conversion rate of 35 to 45%, while the two-stage process is carried out at 105 to 110° C. at 10 bar with a conversion rate of approximately 100%. The selectivities are around 94% in both cases.

It is an object of the present invention to provide suitable catalytically active compositions and also alternative methods for the gas-phase dehydrogenation of primary or secondary alcohols to give the corresponding aldehydes or ketones respectively.

The object is achieved by a method for dehydrogenating primary or secondary alcohols having 1 to 12 carbon atoms to give the corresponding aldehydes or ketones in which the alcohol is brought into contact with a catalytically active composition comprising an active component of the formula $$Pd_aBi_bY_cZ_d,$$

where
Y is selected from the group consisting of Co, Rh, Pt, Ag, Au, and
Z is selected from the group consisting of Na, Cs, Mg, Ca, Ba, V, Cr, W, Fe, Ni, Cu, Sb, and where the indices a, b, c and d give the mass ratios of the respective elements to one another and
a=0.1-3,
b=0.1-3,
c=0-3,
d=0-1.

In an embodiment of the invention the active component has the formula $Pd_aBi_b$, with
a=0.1-3,
b=0.1-3.

Preferably, c=0.1-3, that is the catalyst, in addition to palladium and bismuth, also comprises at least one element of the group consisting of Co, Rh, Pt, Ag and Au and, in addition, optionally also one or more further elements from the group consisting of Na, Cs, Mg, Ca, Ba, V, Cr, W, Fe, Ni, Cu and Sb.

In a preferred embodiment of the invention, the active component has the formula $Pd_aBi_bY_c$, Y being Au or Rh, and
a=0.1-3,
b=0.1-3,
c=0.1-3.

In a further preferred embodiment, the active component has the formula $Pd_aBi_bRh_c$, with
a=0.1-3,
b=0.1-3,
c=0.1-3.

In a further preferred embodiment, the active component has the formula $Pd_aBi_bRh_eY_f$, with Y=Ag or Pt, and
a=0.1-3,
b=0.1-3,
e=0.1-3,
f=0-1,
e+f≦3.

In a further preferred embodiment, the active component has the formula $Pd_aBi_bCo_c$, with
a=0.1-3,
b=0.1-3,
c=0.1-1.

All of the catalytically active compositions listed hitherto can be used both as solid catalysts and also as supported catalysts. In the case of supported catalysts, the active component of the catalytically active composition is applied to a suitable support material.

In the context of the present invention, any support material known to those skilled in the art can be used. Also, the supports can have all geometrical shapes known to those skilled in the art, for example as ropes, rings, extrudates, grains, granules, powders, tablets etc.

Preferred support materials are selected from the group consisting of silicon carbides, silicon nitrides, carbon nitrides, oxonitrides, oxocarbides, bismuth oxide, titanium oxide, zirconium oxide, boron nitride, aluminum oxide, silicates, aluminosilicates, zeolitic and zeolitic-analogous materials, steatite, activated carbon, metal meshes, stainless steel meshes, steel meshes and mixtures of two or more of the abovementioned support materials.

Particularly preferably, as support material, use is made of steatite or silicon carbide. Said ceramic supports can be materials having a large surface area, such as, for example, greater than 100 m²/g. Preferably, however, in the context of the present invention, use is made of supports having small surface areas (less than 100 m²/g), particularly preferably supports having very small surface areas (less than 20 m²/g).

Likewise, in addition to the pure oxide, nitride or carbide supports, use can be made of those support materials to which have been admixed or which comprise basic components, for example magnesium oxide (MgO), calcium oxide (CaO), barium oxide (BaO) or other alkali metal or alkaline earth metal components.

In the context of the present invention, particularly preferably, use is made of support materials of low porosity (specific surface area<20 m²/g), or without porosity.

Preferably, the total loading of the at least one support material with the active component is in the range from 0.1 to 20% by weight, preferably in the range from 8 to 15% by weight, and further preferably in the range from 0.1 to 7% by weight, and also particularly preferably in the range from 0.5 to 4% by weight.

If in the context of the present invention, use is made of steatite as support material, in particular preferably, a total loading of active component of 2 to 4% by weight, for example 3% by weight, is employed.

The index a is in a range from $0.1 \leq a \leq 3$, preferably $0.5 \leq a \leq 2$, and particularly preferably $0.75 \leq a \leq 1.5$. Index b is in the range from $0 \leq b \leq 3$, preferably $0.5 \leq b \leq 2$, and particularly preferably $0.75 \leq b \leq 1.5$.

The index c is in a range from $0 \leq c \leq 3$, preferably $0.1 \leq c \leq 3$, and particularly preferably $0.5 \leq c \leq 2$, and particularly preferably $0.75 \leq c \leq 1.5$. Index d is generally in a range from $0 \leq d \leq 1$, preferably $0 \leq d \leq 0.5$, and particularly preferably $0 \leq d \leq 0.1$, the indices giving the mass ratios of the respective elements to one another respectively in % by weight of the respective elements, based on the mass of the support.

Catalytically active compositions of the formulae below which have an active component of the formulae below have proved particularly advantageous:

$Pd_{0.5-1.0}Rh_{0.5-1.25}Bi_{1.25-1.75}Ag_{0.05-0.15}$ $Pd_{0.5-1.0}Rh_{1.0-1.5}Bi_{0.75-1.25}Pt_{0.01-0.1}$ $Pd_{0.25-0.5}Rh_{1.75-2.5}Bi_{0.25-0.5}Co_{0.01-0.1}$ $Pd_{0.5-1.25}Rh_{0.5-1.25}Bi_{0.75-1.5}Cr_{0.01-0.1}$ $Pd_{1.0-1.75}Rh_{0.25-0.75}Bi_{0.75-1.5}Pt_{0.0-0.15}Co_{0.01-0.1}$ $Pd_{1.0-1.75}Rh_{0.25-0.75}Bi_{0.75-1.5}Pt_{0.05-0.15}$ $Pd_{0.5-1.0}Rh_{1.0-1.75}Bi_{0.5-1.25}Ag_{0.03-0.15}Ca_{0.02-0.1}$ $Pd_{0.4-1.0}Rh_{1.0-1.75}Bi_{0.75-1.25}Ag_{0.03-0.15}$ $Pd_{1.25-1.75}Rh_{1.25-1.75}Co_{0.005-0.02}$ $Pd_{0.4-1.0}Rh_{1.0-1.75}Bi_{0.75-1.25}$ $Pd_{0.15-2.25}Rh_{0.0-2.5}Bi_{0.15-2.75}$

Therein, the indices denote the mass ratios of the individual elements to one another. In particular preference is given to compositions of the abovementioned formulae for which, in addition, a+b+c=3.

Examples of catalytically active compositions which have proved particularly advantageous have an active component of the formula below:

$Pd_{0.75}Rh_{0.75}Bi_{1.5}Ag_{0.1}$;

$Pd_{0.75}Rh_{1.25}Bi_{1}Pt_{0.05}$;

$Pd_{0.325}Rh_{2.25}Bi_{0.375}CO_{0.05}$;

$Pd_{0.85}Rh_{0.85}Bi_{1.25}Cr_{0.05}$;

$Pd_{1.4}Rh_{0.375}Bi_{1.125}Pt_{0.1}Co_{0.05}$;

$Pd_{1.4}Rh_{0.375}Bi_{1.125}Pt_{0.1}$;

$Pd_{0.8}Rh_{1.3}Bi_{0.85}Ag_{0.05}Ca_{0.05}$;

$Pd_{0.6}Rh_{1.33}Bi_{1}Ag_{0.08}$;

$Pd_{1.5}Bi_{1.5}CO_{0.01}$ or $Pd_{0.6}Rh_{1.33}Bi_{1}$

For example, catalytically active compositions which have proved particularly advantageous are those which have an active component of the formula below $Pd_{0.75\%}Rh_{0.75\%}Bi_{1.5\%}Ag_{0.1\%}$;

$Pd_{0.75\%}Rh_{1.25\%}Bi_{1\%}Pt_{0.05\%}$;

$Pd_{0.325\%}Rh_{2.25\%}Bi_{0.375\%}Co_{0.05\%}$;

$Pd_{0.85\%}Rh_{0.85\%}Bi_{1.25\%}Cr_{0.05\%}$;

$Pd_{1.4\%}Rh_{0.375\%}Bi_{1.125\%}Pt_{0.1\%}Co_{0.05\%}$;

$Pd_{1.4\%}Rh_{0.375\%}Bi_{1.125\%}Pt_{0.1\%}$;

$Pd_{0.8\%}Rh_{1.3\%}Bi_{0.85\%}Ag_{0.05\%}Ca_{0.05\%}$;

$Pd_{0.6\%}Rh_{1.33\%}Bi_{1\%}Ag_{0.08\%}$;

$Pd_{1.5\%}Bi_{1.5\%}Co_{0.1\%}$ or $Pd_{0.6\%}Rh_{1.33\%}Bi_{1\%}$;

applied to at least one support material as described above, the indices indicating the mass fractions (% by weight), based on the respective support material.

In addition, catalytically active compositions which have proved particularly suitable for dehydrogenating methanol to formaldehyde and ethanol to acetaldehyde are those of the formula $Pd_{0.15-2.25}Rh_{0-2.5}Bi_{0.15-2.75}$ $Pd_{0.1-1.0}Rh_{1.5-3.0}Bi_{0.1-1.0}$ $Pd_{0.1-1.1}Rh_{1.0-2.6}Bi_{0.1-1.1}$ $Pd_{0.1-1.1}Rh_{1.2-2.8}Bi_{0.1-1.1}$ $Pd_{0.1-1.5}Rh_{1.0-2.99}Bi_{0.1-1.5}$ $Pd_{1.0-2.0}Rh_{0.1-10}Bi_{0.5-2.0}$ These are in particular on steatite as support.

Examples are $Pd_{0.375}Rh_{2.25}Bi_{0.375}$ $Pd_{0.6}Rh_{1.8}Bi_{0.6}$ $Pd_{0.45}Rh_{2.1}Bi_{0.45}$ $Pd_{0.5}Rh_{2.0}Bi_{0.5}$ $Pd_{1.5}Rh_{0.375}Bi_{1.125}$.

In addition, catalytically active compositions which have proved particularly suitable for dehydrogenating methanol to formaldehyde and ethanol to acetaldehyde are those of formulae $Pd_{0.4-1.0}Rh_{1.0-1.75}Bi_{0.75-1.25}Ag_{0.03-0.15}$ $Pd_{1.25-1.75}Rh_{1.25-1.75}Co_{0.005-0.02}$ $Pd_{0.2-1.0}Bi_{0.6-1.4}Rh_{0.93-1.73}Ag_{0.01-0.20}$ $Pd_{1.0-2.0}Bi_{1.0-2.0}Co_{0.005-0.15}$ $Pd_{1.0-2.0}Bi_{1.0-2.0}Pt_{0.05-0.15}$ $Pd_{0.7-1.7}Rh_{0.3-1.5}Bi_{0.3-1.5}Co_{0.05-0.15}$.

These are in particular on steatite as support.
Examples are $Pd_{0.6}Bi_1Rh_{1.33}Ag_{0.08}$ $Pd_{1.5}Bi_{1.5}Co_{0.01}$ $Pd_{1.5}Bi_{1.5}Pt_{0.1}$ $Pd_{1.2}Rh_{0.9}Bi_{0.9}Co_{0.1}$ In addition, catalytically active compositions which have proved particularly suitable for dehydrogenating methanol to formaldehyde, and ethanol to acetaldehyde, are those of the formulae $Pd_{0.5-2.0}Rh_{0.1-1.1}Bi_{0.5-2.0}$ $Pd_{1.0-2.0}Rh_{0.1-1.0}Bi_{0.5-2.0}$ $Pd_{1.0-2.5}Rh_{0.01-0.5}Bi_{0.5-1.75}$ $Pd_{0.1-1.5}Rh_{0.5-1.75}Bi_{1.25}Pt_{0.001-0.1}$ These are, in particular, on steatite as support.
Examples are $Pd_{1.2}Rh_{0.6}Bi_{1.2}$ $Pd_{1.5}Rh_{0.375}Bi_{1.125}$ $Pd_{1.8}Rh_{0.15}Bi_{1.05}$ $Pd_{0.75}Rh_1Bi_{1.25}Pt_{0.05}$ In a particularly preferred embodiment, the above-listed active components are applied to steatite, silicon carbide or a mixture of the two as support material.

Fundamentally, solid catalysts used according to the invention can be prepared according to all preparation methods for solid catalysts known to those skilled in the art. The preferred mode of preparation is co-precipitation. In this method one, two or more elements from the group of the active components are mixed as aqueous salt solutions and then precipitated together in the form of their hydroxides or carbonates. This produces an amorphous or else crystalline precipitate or a gel. If appropriate, the resultant precipitate can be washed salt free. The resultant product is dried in a following method step. If appropriate the dried solid can additionally be ground for improved homogenization of the product. Likewise, the solid, if appropriate, can further be shaped, in the context of shaping, the present product being able, if appropriate, to be plasticized by kneading and extruded to form strands, or else, after admixture of aids, pressed to form tablets. Subsequently, the dried product is calcined.

The calcined product can if appropriate be activated and if appropriate be tested for its catalytic properties such as selectivity and activity, and also stability. The testing can proceed according to all methods known to those skilled in the art, such as, for example, use of samples of a catalyst in selected reactions and analysis of its catalytic properties.

The method for preparing the solid catalysts thus has the following steps:
(i) precipitating out the at least one active component from a solution comprising one of its salts;
(ii) drying the product prepared in step (i);
(iii) calcining the product dried in step (ii);
(iv) if appropriate testing the product calcined in step (iii).

Preferably, in the context of the present invention, impregnating the support body below the water uptake of the support ("incipient wetness") or adsorption from supernatant solution, or application of thin layers to ceramic support materials are used as synthesis routes for preparing supported catalysts.

Generally, in the context of all methods mentioned, the elements of the active component are used as thermally unstable salts such as, for example, nitrates, acetates, carbonates or hydroxides. In the context of impregnation from supernatant solution, the support is dipped into the solution which comprises the elements of the respective active component in the form of its anions, and treated under exactly defined conditions with respect to concentration, mixing, temperature and time. To increase the effectiveness of impregnation, if appropriate, the air in the support pores can be removed by evacuation or the support can be treated with gas before impregnation. The impregnation step is generally followed by a drying and calcination step.

In the synthesis route via the application of thin layers to ceramic support materials, the respective precursor solutions can be applied to the support sequentially one at a time or preferably as a mixture together. In this case, preferably, use is made of the thermally unstable anions of the respective elements which the active component comprises in accordance with the statements above. Application can be carried out by simple delivery from a pipette, or else via spraying, spray-freeze drying, and all other techniques known in this context to those skilled in the art. It is likewise possible, using spray-freeze drying as described in DE 102 11 260.6, to apply thin layers of the respective elements of the catalytically active composition to a desired support.

After application of the precursor solution, generally a drying step follows. In the context of this drying step, the materials are dried for between 30 minutes and 24 hours at temperatures between 40° C. and 150° C. Preferably, the materials are dried for 3 hours at 80° C. Likewise preference is given to freeze drying the materials in vacuum or under reduced pressure.

The drying step is generally followed by a calcination step. Calcination is generally taken to mean a heat treatment in an oxidizing atmosphere at temperatures generally above the later service temperatures of the catalytically active composition. In the context of the present invention, in this case, the materials are heated between 1 and 100 hours at a heating rate in the range from 0.25° C./min to 10° C./min to a final temperature between 200° C. and 1200° C. and kept at the selected temperature for between 30 min and 150 hours. In the context of the present invention, a ramp of 3° C./min, a final temperature of 550° C. and also a holding time of 3 hours are preferred. As calcination atmosphere, air, $N_2$, forming gas ($H_2$ in $N_2$, for example 5% $H_2$ in $N_2$), reactive gases ($Cl_2$, $NH_3$ and others) or vacuum may be used. Preferably, calcination is carried out under air or $N_2$.

Accordingly, the preferred method for preparing a catalytically active composition comprising at least one active component applied to at least one support material comprises at least the following steps:
(α) applying a solution comprising at least one active component to at least one support material;
(β) drying the product prepared in step (α);
(χ) calcining the product dried in step (β);
(δ) if appropriate testing the product calcined in step (χ).

In a further step, the catalytically active compositions can be tested for their catalytic properties.

The catalytically active compositions prepared in the context of this invention are tested by installation of, for example, at least 1 ml of the material to be tested into a stainless steel reactor known to those skilled in the art. After the catalytic reaction inside the reactor, the subsequent product gas analysis can be carried out by all analytical methods known therefor to those skilled in the art, for example by GC/MS having an HP-5-MS column, for separation and determination of the products and starting materials.

Preferably, the inventive method is used for dehydrogenating methanol to give formaldehyde, and ethanol to give acetaldehyde. In addition, it can be used for dehydrogenating 1-propanol to give propionaldehyde, isopropanol to give acetone, 1-butanol to give butyraldehyde, 2-butanol to give methyl ethyl ketone, isobutanol to give isobutyraldehyde, and also for dehydrogenating the isomeric primary and secondary pentanols, hexanols, heptanols, octanols, nonanols, decanols, undecanols and dodecanols to give the corresponding aldehydes and ketones respectively. Preferably, the $C_1$-$C_6$-alkanols are dehydrogenated, in particular said $C_1$-$C_4$-alkanols.

Particularly preferably, the dehydrogenation is carried out in the presence of oxygen.

In a further preferred embodiment of the present invention, the dehydrogenation of hydrocarbons using a catalytically active composition as described above is carried out in the presence of oxygen and steam.

The oxygen content in the dehydrogenations which are carried out at least in the presence of oxygen, or oxygen and water, is, in the context of the present invention, in the ratio to the total volume of the fed starting materials, in the range from 1% by volume to 50% by volume, preferably in the range from 1% by volume to 30% by volume, and particularly preferably in the range from 1% by volume to 10% by volume, or from 20 to 30% by volume.

The water content in dehydrogenations which are carried out at least in the presence of oxygen and hydrogen is in the ratio to the total volume of the fed starting materials in the range up to 50% by volume, preferably in the range from 1% by volume to 35% by volume, particularly preferably in the range from 5% by volume to 25% by volume. If appropriate, in the above-described dehydrogenations, nitrogen can be fed as balance gas.

The alcohol content in dehydrogenations which are carried out as described above is, based on the total volume of the fed starting materials, in the range from 0 to 90% by volume, preferably in the range from 0.01 to 25% by volume, particularly preferably in the range from 0.1 to 30% by volume, for example from 0.1 to 4% by volume or from 15 to 25% by volume.

The molar ratio of alcohol to oxygen in the context of the present invention is generally in range from 3:1 to 1:20, preferably in a range from 1:1 to 1:7, particularly preferably in a range from 1:2 to 1:5.

The molar ratio of alcohol to water in the context of the inventive method is in a range from 3:1 to 1:50, preferably in a range from 1:5 to 1:40, particularly preferably in a range from 1:10 to 1:30.

The inventive catalytic compositions used are distinguished in that they make dehydration possible even at relatively low temperatures of significantly below 400° C.

The catalyst activity remains virtually unchanged over a long time, so that reactivation is only seldom required.

The reaction temperatures are in a range between generally 150° C. and 450° C., preferably between 150 and 350° C., particularly preferably between 200 and 300° C., and especially between 210 and 260° C.

The respective gas space velocity (GHSV) is in a range between 100 $h^{-1}$ and 100 000 $h^{-1}$, preferably between 1000 $h^{-1}$ and 10 000 $h^{-1}$.

For dehydrogenating ethanol to give acetaldehyde, the following reaction conditions have inter alia proved particularly expedient: the reaction takes place at a temperature between 200 and 300° C., preferably between 210 and 260° C. The space velocity (GHSV) is between 100 and 50 000 $h^{-1}$, preferably between 1000 and 10 000 $h^{-1}$. The ethanol content in the feed gas stream is between 0.1% by volume and 15% by volume, preferably between 1% by volume and 10% by volume. The ethanol:oxygen molar ratio in the feed gas stream is from 10:1 to 1:5. The feed gas stream can comprise up to 20% by volume of water, preferably from 0.1 to 10% by volume of water.

The dehydrogenation catalyst can be arranged fixedly in the reactor, or used, for example, in the form of a fluidized bed, and have a corresponding shape. Suitable shapes, are, for example, those such as chips, tablets, monoliths, beads or extrudates (strands, cartwheels, stars, rings).

A suitable reactor form is the fixed-bed tubular reactor or tube-bundle reactor. In these the catalyst is situated as a fixed bed in a reaction tube or in a bundle of reaction tubes. The reaction tubes are customarily heated indirectly by burning, in the space surrounding the reaction tubes, a gas, for example a hydrocarbon such as methane, or by using a heat carrier medium (salt bath, recirculated gas etc.). The reaction tubes can also be heated electrically using heating jackets. Customary reaction tube inner diameters are about 1 to 15 cm. A typical dehydrogenation tube bundle reactor comprises approximately 10 to 32 000 reaction tubes.

Generally, the catalytically active composition is regenerated by burning off, in the presence of oxygen, the coke deposited on the catalyst surface. For this purpose, air or oxygen, which can be diluted with inert gases, is added to the feed gas stream which comprises the compound to be dehydrogenated, its content in the gas stream being able to be reduced during regeneration to 0% by volume. The regeneration is carried out at a temperature of generally 200 to 400° C.

In a variant of the regeneration, the inventive catalytically active composition is first burnt off at temperatures from 200 to 400° C., preferably from 250 to 350° C., in a period from 1 min to 100 h, preferably 10 min to 24 h, particularly preferably 30 min to 1.5 h, so that the coke deposited on the catalyst surface is burnt off to carbon dioxide.

Preferably, the burnoff in the context of the present invention is carried out at a temperature of 350° C. in an atmosphere of about 1% oxygen in nitrogen, preferably 5% oxygen in nitrogen, particularly preferably about 10% oxygen in nitrogen.

After the burnoff, the atmosphere surrounding the catalytically active composition is purged with nitrogen so as to be oxygen-free.

As a third step in the context of the regeneration, a hydrogen treatment of the catalytically active composition is performed. This is preferably carried out at temperatures in the range from 220 to 280° C., particularly preferably 250 to 270° C., in the presence of forming gas. Particularly preferably, use is made of forming gas having a composition of about 3% hydrogen in nitrogen. The hydrogen treatment is performed in a period of 1 min to 100 h, preferably 10 min to 24 h, particularly preferably 30 min to 1.5 h.

Subsequently to this, the atmosphere surrounding the catalytically active composition is purged so as to be hydrogen-free.

The present invention will be explained hereinafter by examples.

The examples show the preparation of various catalytically active compounds and also their testing for catalytic properties.

If, in the context of the individual examples, nothing to the contrary is stated, for the testing 1 ml of the respective catalytically active composition is used.

EXAMPLES

General Preparation Protocol For The Catalysts

As support, use is made of spherical steatite (Ceram Tek, 4-5 mm, 83577). In all cases use is made of, as Pd precursor, $Pd(NO_3)_2 \cdot H_2O$, as Bi precursor $Bi(NO_3)_3 \cdot 5H_2O$ and, as Rh precursor, an Rh solution comprising 13.7% by weight of Rh. Because of the solubility behavior of the Pd and Bi precursors, 65% strength by weight nitric acid ($HNO_3$) was used as solvent for these two precursors. During the preparation of materials comprising one of these metals or both metals and, in addition, Rh, the precursors were first dissolved in gently warmed $HNO_3$ and stirred until complete dissolution, followed by addition of the Rh solution.

The resultant mixture was subsequently added dropwise to the steatite by pipette, stirring being performed by a magnetic stirrer. After addition of the entire solution, the mixture was further stirred for 2 minutes, in order to ensure a homogeneous coating of the steatite support with the catalyst metal precursors. When excess solution was used, the steatite was stirred and gently heated until the entire solution had evaporated. After impregnation, the catalysts were dried for 16 h at 80° C. in a nitrogen stream and subsequently calcined for 3 h at 550° C. in the nitrogen stream, the temperature ramp being 5° C./min.

General Test Protocol

To test the catalysts, 42.6 ml of the respective catalyst were charged into a stainless steel tubular reactor which was immersed in a salt bath. The reaction temperature was controlled via the salt bath temperature. The stainless steel reactor itself had inert behavior under the reaction conditions. The reaction products were analyzed by gas chromatography, using a GC system of the Agilent 6890 series. The gas-phase products were analyzed using a Crompack 7574 capillary column and an online gas analyzer (Ultramat 23 from Siemens) which was equipped with CO, $CO_2$ and $O_2$ sensors. The liquid products were analyzed by means of a Restek 10193 capillary column.

Before the test, all catalysts were heated for 20 minutes at the reaction temperature in the nitrogen stream.

Example 1

Pd on Steatite

The impregnation solution comprised 1.63 g of $Pd (NO_3)_2 \cdot H_2O$ in 8 ml of $HNO_3$.

The oxidative dehydrogenation of ethanol was carried out at a gas space velocity of 7300 $h^{-1}$ (2.6% ethanol, 2.6% $O_2$ and 6.4% $H_2O$ in nitrogen) at a temperature of 220° C. The ethanol conversion rate was 12.5%, the selectivity to acetaldehyde 66.5%, equivalent to an acetaldehyde yield of 8.3%.

When the reaction was carried out at 260° C. using 3.8% ethanol, 3.7% $O_2$ and 7.4% $H_2O$ in nitrogen, an ethanol conversion rate of 19.2% was obtained at a selectivity to acetaldehyde of 20.0%, equivalent to an acetaldehyde yield of 11.9%.

Example 2

Bi on Steatite (0.375% by Weight)

The impregnation solution comprised 1.75 g of $Bi (NO_3)_3 \cdot 5H_2O$ in 8 ml of $HNO_3$. The oxidative dehydrogenation of ethanol was carried out at a gas space velocity of 7300 $h^{-1}$ using 3.8% ethanol, 3.7% $O_2$ and 7.3% $H_2O$ in nitrogen at 220 and 260° C. An ethanol conversion rate was not observed.

Example 3

Pd—Bi on Steatite (Total Loading: 0.75% by Weight)

The impregnation solution comprised 1.64% by weight of Pd(III) nitrate, equivalent to 0.375% by weight metal and 1.75% by weight Bi(III) nitrate, equivalent to 0.375% by weight metal. The oxidative dehydrogenation of ethanol was carried out at a gas space velocity of 7300 $h^{-1}$ using 3.8% ethanol, 3.7% $O_2$ and 7.3% $H_2O$ in nitrogen. At 220° C., an ethanol conversion rate of 48.4% was achieved, and a selectivity to acetaldehyde of 9.6%, equivalent to a yield of 4.6%.

Example 4

Rh on Steatite

The impregnation solution comprised 33.6 g of rhodium solution, equivalent to 4.6 g of rhodium. The oxidative dehydrogenation of ethanol was carried out at a gas space velocity of 7300 $h^{-1}$ using 3.8% ethanol, 3.7% $O_2$ and 7.3% $H_2O$ in nitrogen. At 220° C., a conversion rate of 41.9% was achieved at a selectivity to acetaldehyde of 10.6%, equivalent to a yield of 4.4%.

Example 5

Rh—Bi on Steatite (Total Loading: 2.63% by Weight)

The impregnation solution comprised 0.77 g of the Bi precursor in 3 ml of $HNO_3$ and 33.7 g of the Rh precursor solution. The oxidative dehydrogenation of ethanol was carried out at a gas space velocity of 7300 $h^{-1}$ using 3.8% ethanol, 3.7% $O_2$ and 7.3% $H_2O$ in nitrogen. At 220° C., a conversion rate of 10.1% was obtained. At 280° C., a conversion rate of 85.7% was achieved.

Example 6

Pd—Rh on Steatite

The impregnation solution comprised 0.37 g of the Pd precursor in 3 ml of $HNO_3$ and 33.7 g of the Rh precursor solution. The oxidative dehydrogenation of ethanol was carried out at a gas space velocity of 7300 $h^{-1}$ using 3.8% ethanol, 3.7% $O_2$, 7.3% $H_2O$ in nitrogen. At 220° C., an ethanol conversion rate of 48.4% was obtained at a selectivity to acetaldehyde of 9.6%, equivalent to a yield of 4.6%.

Example 7

Pd—Bi—Co on Steatite (Total Loading: 3% by Weight)

The impregnation solution comprised 6.7 g, equivalent to 1.5% by weight of the Pd precursor, 7.036 g, equivalent to 1.5% by weight, of the Bi precursor and 0.1 g, equivalent to 0.01% by weight, of $Co(NO_3)_2$. The oxidative dehydrogenation of ethanol was carried out at a gas space velocity of 7300 $h^{-1}$ using 3.8% ethanol, 3.7% $O_2$, 7.3% $H_2O$ in nitrogen. The results of the experiments are summarized in table 1.

TABLE 1

| Temperature [° C.] | Conversion rate [%] | Yield [%] | Selectivity [%] |
|---|---|---|---|
| 210 | 76.6 | 68.4 | 89.3 |
| 220 | 98.0 | 78.5 | 80.1 |
| 260 | 98.4 | 78.0 | 79.3 |

Example 8

Pd—Bi—Rh on Steatite (Total Loading: 3% by Weight)

The impregnation solution comprised 1.67 g of the Pd precursor, equivalent to 0.38% by weight, 1.83 g of the Bi precursor, equivalent to 0.38% by weight, and 33.9 g of $Rh(NO_3)_3$ solution, equivalent to 2.25% by weight.

The experimental conditions and experimental results are given in the table below.

TABLE 2

| Temperature [° C.] | GHSV [$h^{-1}$] | EtOH [%] | $O_2$ [%] | $H_2O$ [%] | Conversion rate [%] | Yield [%] | Selectivity [%] |
|---|---|---|---|---|---|---|---|
| 220 | 7316 | 3.8 | 4.0 | 7.4 | 93.8 | 87.2 | 93.0 |
| 240 | 7316 | 3.8 | 3.7 | 7.4 | 99.5 | 82.6 | 83.0 |
| 260 | 7316 | 3.8 | 3.7 | 7.4 | 99.5 | 78.2 | 78.6 |

Example 9

Dependence of Catalytic Activity on Oxygen Concentration

The material from example 8 was tested at a gas space velocity of 7316 $h^{-1}$ using 4.96% ethanol, 3.5% $H_2O$ and various oxygen concentrations in nitrogen at 220° C. The results are given in the table below.

TABLE 3

| $O_2$/EtOH molar ratio | Conversion rate [%] | Yield [%] | Conversion rate [%] |
|---|---|---|---|
| 0.4 | 73.1 | 73.0 | 100.0 |
| 0.6 | 94.5 | 89.5 | 91.8 |
| 0.8 | 99.9 | 81.8 | 82.0 |
| 1.0 | 100.0 | 73.9 | 73.9 |

Example 10

Dependence of Catalytic Activity on $H_2O$ Concentration

The material from example 8 was tested at a gas space velocity of 7316 $h^{-1}$ using 3.8% ethanol and an $O_2$/EtOH ratio of 1.1:1 and various steam concentrations in nitrogen at 220° C. The results are summarized in the table below.

TABLE 4

| $H_2O$ [%] | Conversion rate [%] | Yield [%] | Selectivity [%] |
|---|---|---|---|
| 0.73 | 97.7 | 90.6 | 92.8 |
| 4.0 | 95.0 | 89.9 | 94.7 |
| 7.4 | 93.8 | 87.2 | 93.0 |

Example 11

Dependence on Ethanol Concentration

The material from example 8 was tested at a gas space velocity of 7316 $h^{-1}$ using 1% $H_2O$ and an $O_2$/EtOH ratio of 0.72:1 in nitrogen at 220° C. The results are summarized in the table below.

TABLE 5

| EtOH [%] | Conversion rate [%] | Yield [%] | Selectivity [%] |
|---|---|---|---|
| 4.5 | 99.8 | 88.0 | 88.2 |
| 5.6 | 99.4 | 85.4 | 86.0 |
| 6.5 | 98.3 | 85.7 | 87.1 |
| 7.4 | 98.0 | 85.1 | 86.8 |

The invention claimed is:

1. A method for thermally dehydrogenating an alcohol selected from the group consisting of methanol and ethanol to give the corresponding aldehydes in the gas phase, wherein dehydrogenation is effected by bringing the alcohol at a temperature ranging from 150° C. to 450° C. into contact with a catalytically active composition comprising an active component of the formula:

$Pd_a Bi_b Y_c Z_d$, where
Y is selected from the group consisting of Co, Rh, Pt, Ag, and Au;
Z is selected from the group consisting of Na, Cs, Mg, Ca, Ba, V, Cr, W, Fe, Ni, Cu, and Sb;
where the indices a, b, c and d give the mass ratios of the respective elements to one another, where
a=0.1-3,
b=0.1-3,
c=0.01-3,
d=0-1.

2. The method according to claim 1, wherein the active component has the formula:

$Pd_a Bi_b Y_c$, with Y=Au or Rh, where
a=0.1-3,
b=0.1-3,
c=0.01-3.

3. The method according to claim 1, wherein c ranges from 0.1 to 3.

4. The method according to claim 1, wherein the active component has the formula:

$Pd_a Bi_b Rh_c$, where
a=0.1-3,
b=0.1-3,
c=0.1-3.

5. The method according to claim 1, wherein the active component has the formula:

$Pd_a Bi_b Rh_c Y_f$, with Y =Ag or Pt, where
- a=0.1-3,
- b=0.1-3,
- e=0.1-3,
- f=0-1,
- e+f<3.

6. The method according to claim 1, wherein the active component has the formula:

$$Pd_aBi_bCo_c,$$

where
- a=0.1-3,
- b=0.1-3,
- c=0.1-1.

7. The method according to claim 1, wherein the active component has one of the formulae below:

$$Pd_{0.5-1.0}Rh_{0.5-1.25}Bi_{1.25-1.75}Ag_{0.05-0.15}$$

$$Pd_{0.5-1.0}Rh_{1.0-1.5}Bi_{0.75-1.25}Pt_{0.01-0.1}$$

$$Pd_{0.25-0.5}Rh_{1.75-2.5}Bi_{0.25-0.5}Co_{0.01-0.1}$$

$$Pd_{0.5-1.25}Rh_{0.5-1.25}Bi_{0.75-1.5}Cr_{0.01-0.1}$$

$$Pd_{1.0-1.75}Rh_{0.25-0.75}Bi_{0.75-1.5}Pt_{0.0-0.15}Co_{0.01-0.1}$$

$$Pd_{1.0-1.75}Rh_{0.25-0.75}Bi_{0.75-1.5}Pt_{0.05-0.15}$$

$$Pd_{0.5-1.0}Rh_{1.0-1.75}Bi_{0.5-1.25}Ag_{0.03-0.15}Ca_{0.02-0.1}$$

$$Pd_{0.4-1.0}Rh_{1.0-1.75}Bi_{0.75-1.25}Ag_{0.03-0.15}$$

$$Pd_{0.4-1.0}Rh_{1.0-1.75}Bi_{0.75-1.25}$$

$$Pd_{0.15-2.25}Rh_{0-2.5}Bi_{0.15-2.75}.$$

8. The method according to claim 1, wherein the active component is present on a support material selected from the group consisting of silicon carbides, silicon nitrides, carbon nitrides, oxonitrides, oxocarbides, bismuth oxide, titanium oxide, zirconium oxide, boron nitride, aluminum oxide, silicates, aluminosilicates, zeolitic materials, zeolite-analogous materials, steatite, activated carbon, metal meshes, stainless steel meshes, steel meshes and mixtures of two or more of the abovementioned support materials.

9. The method according to claim 1, wherein the dehydrogenation is carried out in the presence of oxygen.

10. The method according to claim 1, wherein the dehydrogenation is carried out in the presence of oxygen and steam.

11. The method according to claim 1, wherein methanol is dehydrogenated.

12. The method according to claim 1, wherein ethanol is dehydrogenated.

* * * * *